United States Patent [19]

Tronc

[11] 4,322,622

[45] Mar. 30, 1982

[54] DEVICE FOR THE ACHROMATIC MAGNETIC DEFLECTION OF A BEAM OF CHARGED PARTICLES AND AN IRRADIATION APPARATUS USING SUCH A DEVICE

[75] Inventor: Dominique Tronc, Buc, France

[73] Assignee: C.G.R. MeV, Buc, France

[21] Appl. No.: 136,820

[22] Filed: Apr. 3, 1980

[30] Foreign Application Priority Data

Apr. 3, 1979 [FR] France ............................. 79 08370

[51] Int. Cl.³ ........................ G21K 1/08; H05H 00/00
[52] U.S. Cl. ........................... 250/396 ML; 313/361.1; 315/111.81
[58] Field of Search ............. 313/361; 250/396 ML; 315/111.8

[56] References Cited

U.S. PATENT DOCUMENTS

| | | | |
|---|---|---|---|
| 3,967,225 | 6/1976 | Heighway | 313/361 |
| 4,006,422 | 2/1977 | Schriber | 315/5.41 |
| 4,191,887 | 3/1980 | Brown | 250/396 ML |
| 4,243,916 | 1/1981 | Leboutet et al. | 313/361 |

Primary Examiner—Harold A. Dixon
Attorney, Agent, or Firm—Oblon, Fisher, Spivak, McClelland & Maier

[57] ABSTRACT

An achromatic magnetic deflection device for deflecting by an angle $\phi$ between $\pi$ and $2\pi$ a beam of charged accelerated particles having different momentum. This device comprises an electromagnet provided with pole pieces delimiting three contiguous sectors, the whole of these sectors, having an axis of symmetry XX, presenting flat input E and output S faces and common faces $F_1$ and $F_2$ in an arc of a circle, the position, the radius of curvature of these faces $F_1$, $F_2$ as well as the value of the magnetic induction in the sectors being chosen so that the different paths are substantially orthogonal both to faces $F_1$, $F_2$ and to axis XX.

10 Claims, 11 Drawing Figures

4,322,622

DEVICE FOR THE ACHROMATIC MAGNETIC DEFLECTION OF A BEAM OF CHARGED PARTICLES AND AN IRRADIATION APPARATUS USING SUCH A DEVICE

BACKGROUND OF THE INVENTION

The present invention relates to an achromatic magnetic deflection device for deflecting by an angle $\phi$ a beam of charged accelerated particles (electrons for example), these particles being able to present a large range of moments of quantities of movement.

The deflection device of the invention enables in particular a beam of electrons accelerated between 10 and 20 Mev for example to be deflected by an angle $\phi > \pi$, without having to modify the values of the magnetic fields created in the air gaps of the pole pieces forming part of the deflection device.

SUMMARY OF THE INVENTION

It is an object of the invention to provide a device for the achromatic magnetic deflection of a beam of accelerated charged particles comprising at least one electromagnet having pole pieces delimiting air gaps in which are created magnetic fields having the same direction and specific values so that the paths of the particles have the form of loops whose lengths depend on the momentum of the particles, these pole pieces delimiting a first, a second and a third magnetic sector disposed one after the other and joined together, the whole of these magnetic sectors having a plane of symmetry perpendicular to the plane of the mean path of the beam of particles and intersecting this plane along an axis XX, the magnetic deflection device presenting successively to the beam of particles a flat input face, a first curved face, a second curved face and a flat output face, the input and output flat faces forming therebetween an angle $2\alpha$, the first and second curved faces, as well as the axis of symmetry XX, being substantially orthogonal to the different paths of the particles, the values of the magnetic inductions created in the first and third magnetic sectors being respectively equal to $KB_o$, $B_o$ being the value of the magnetic induction in the second magnetic sector and K a numeric coefficient less than 1.

The above and other objects, features and advantages of the present invention will become apparent from the following description, given solely by way of non-limiting illustration, when taken in conjunction with the accompanying drawings.

DESCRIPTION OF THE PREFERRED EMBODIMENTS

Figure 1:
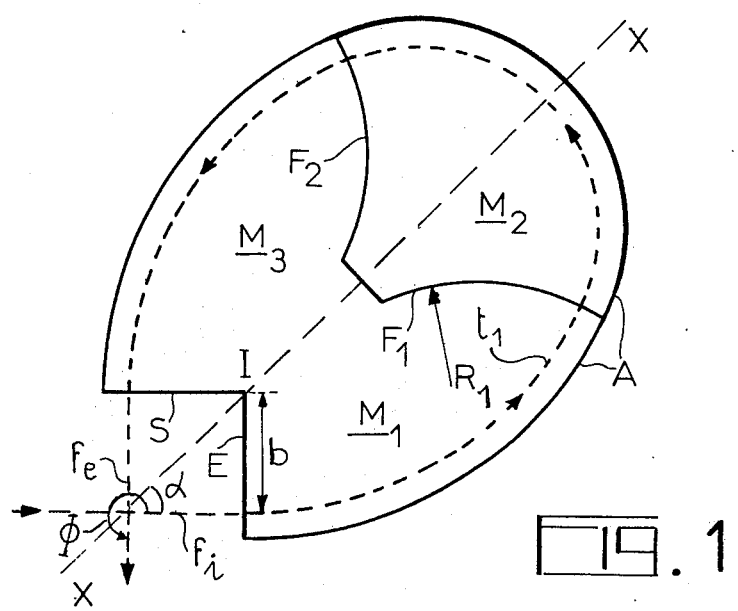
FIG. 1 shows a first embodiment of a magnetic deflection device according to the invention.

The achromatic magnetic deflection device according to the invention, such as shown in FIG. 1, for deflecting by 270° a beam of charged particles, in particular electrons, is formed by an electromagnet having magnetic coils (not visible in the figure) and comprising a pair of pole pieces A, A (only one pole piece A is visible in the figure) of such a shape that they delimit three magnetic sectors $M_1$, $M_2$, $M_3$ having a plane of symmetry perpendicular to the plane in which move the mean paths of the beam of particles and intersecting this plane along an axis XX inclined by an angle $\alpha = \pi/4$ in relation to the mean path of the incident beam $f_i$. The magnetic sector $M_1$ is delimited by a flat input face E and a face $F_1$ substantially circular in shape, with a radius of curvature R, the magnetic sector $M_3$ is delimited by a flat output face S and a face $F_2$ identical to face $F_1$ and the intermediate contiguous magnetic sector $M_2$ being delimited by faces $F_1$ and $F_2$. The input E and output S faces form therebetween an angle $2\alpha = \pi/2$.

Figure 2:
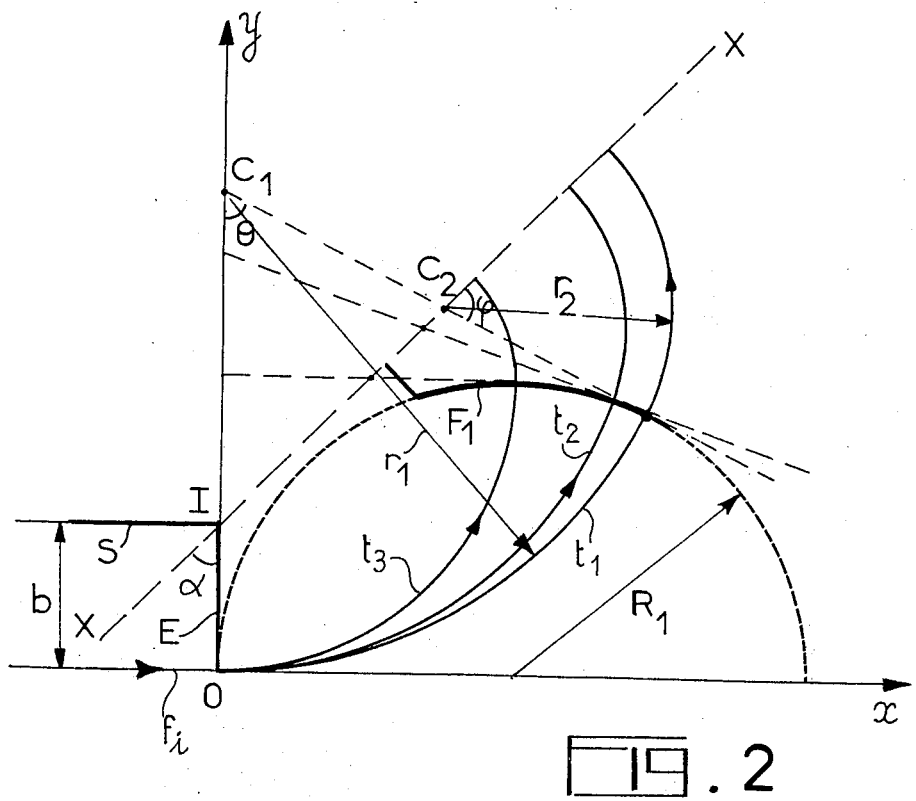
FIG. 2 shows the paths of the particles in the embodiment of FIG. 1.

The heights of the air gaps of magnetic sectors $M_1$ and $M_3$ on the one hand, and $M_2$ on the other are such that the values of the magnetic inductions created respectively in these magnetic sectors $M_1$, $M_2$, $M_3$ are equal to $B_o/2$, $B_o$, $B_o/2$, the particles then being deflected by an angle $\theta$ in each of the magnetic sectors $M_1$ and $M_3$ and by an angle $2\phi$ in magnetic sector $M_2$, the sum $2\theta + 2\phi$ of these angles being equal to $2\pi - 2\alpha = 3\pi/4$ (FIG. 2).

FIG. 2 shows the paths $t_1$, $t_2$ and $t_3$ of the particles having respectively an energy $E_1$, $E_2$, $E_3$. The path $t_1$ has a center of curvature $C_1$ in magnetic sector $M_1$ and a center of curvature $C_2$ in magnetic sector $M_2$. This path $t_1$ is orthogonal on the one hand to faces $F_1$, $F_2$ and to the axis of symmetry XX of the device. In the magnetic deflection device of the invention, the center of curvature $C_2$ of the paths in magnetic sector $M_2$ must be situated on the axis of symmetry XX of the deflection device. This center of curvature $C_2$ of the paths may be defined, in an orthonormed plane xy, such as shown in FIG. 2, by the relationships:

$$x_{C_2} = (r_1 - r_2) \sin \theta \qquad (1)$$

$$y_{C_2} = r_1(1 - \cos \theta) + r_2 \cos \theta$$

$r_1$ being the radius of curvature of the paths in magnetic sector $M_1$ (and in magnetic sector $M_3$ not shown) and $r_2$ being the radius of curvature of the paths in magnetic sector $M_2$.

So that the centers of curvature $C_2$ are situated on the axis of symmetry XX, the following relationship must be verified:

$$r_1 (1 - \cos \theta) + r_2 \cos \theta = \frac{1}{\tan \alpha} (r_1 - r_2) \sin \theta + b \qquad (3)$$

If we assume: $(r_2/r_1) = K$, the relationship (3) becomes $$1 - \cos \theta + K \cos \theta = \frac{1}{\tan \alpha} (1 - K) \sin \theta + \frac{b}{r_1} \qquad (4)$$

but:

$$K = 1 + \frac{\frac{b}{R}\left(tg\frac{\theta}{2} - 1\right)\tan\alpha}{\cos\theta\tan\alpha + \sin\theta} \quad (5)$$

R being the radius of curvature of faces $F_1$, $F_2$.
The value of K is then given by the relationship:

$$r_1 = \frac{R}{\tan\frac{\theta}{2}}, \text{ so } \frac{b}{r_1} = \frac{b}{R}\tan\frac{\theta}{2}.$$

Figure 5:
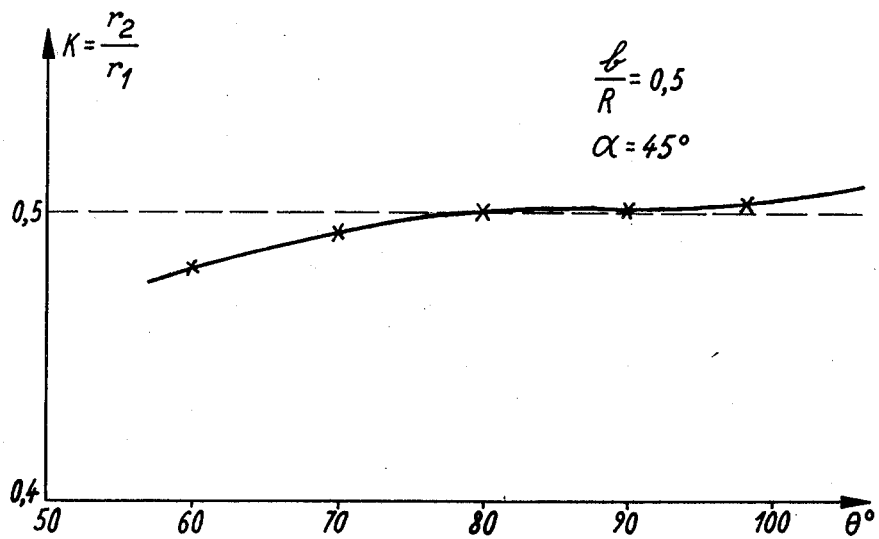
FIGS. 5 and 6 show respectively the variation of the ratio K of the radii of curvature of the different paths for the embodiments shown in FIGS. 1 and 3.

FIG. 5 shows the variation of K as a function of $\theta$, for $\alpha=45°$, (b/R)=0.5. It is to be noted that K is substantially equal to 0.5 for values of $\theta$ between 75° and 100°, which corresponds to an energy range between 1.4 $E_0$ and 0.8 $E_0$.

Figure 3:
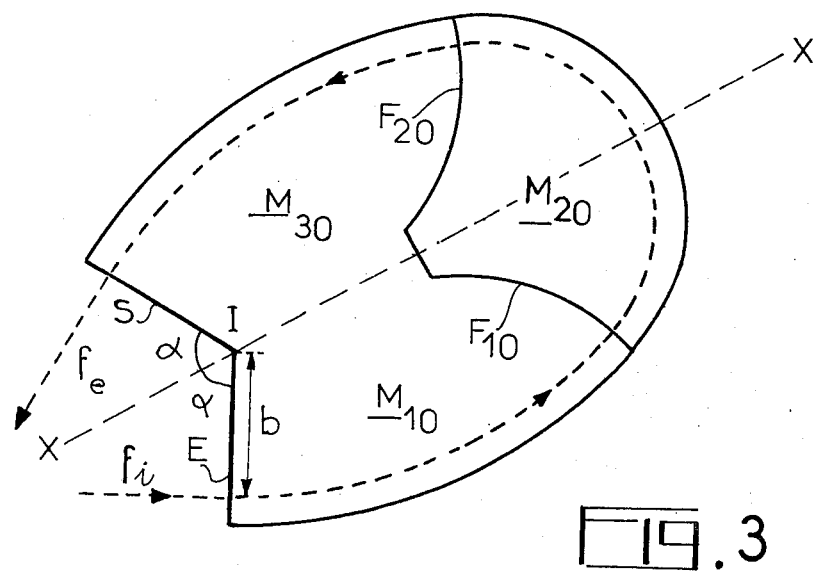
FIG. 3 shows a second embodiment of a magnetic deflection device according to the invention.

FIG. 3 shows another embodiment of a magnetic deflection device in accordance with the invention for deflecting the incident beam $f_i$ by an angle $2\alpha$ equal to 240°, this deflection being achromatic. This magnetic deflection device comprises an electromagnet having magnetic coils (not shown) and provided with a pair of pole pieces of a shape and dimensions such that they delimit three contiguous magnetic sectors $M_{10}$, $M_{20}$, $M_{30}$. Magnetic sector $M_{10}$ presents to the beam a flat input face E and a face $S_{10}$ having the form of an arc of a circle with radius $R_{10}$, magnetic sector $M_{30}$ has a flat output face S and a face $S_{20}$ identical to face $S_{10}$, whereas magnetic sector $M_{20}$ contiguous to magnetic sectors $M_{10}$, $M_{30}$ is delimited by faces $S_{10}$ and $S_{20}$. The heights of the air gaps of magnetic sectors $M_{10}$, $M_{20}$ and $M_{30}$ are such that the magnetic inductions created in each of these sectors are respectively equal to $KB_o$, $B_o$ and $KB_o$.

Figure 4:
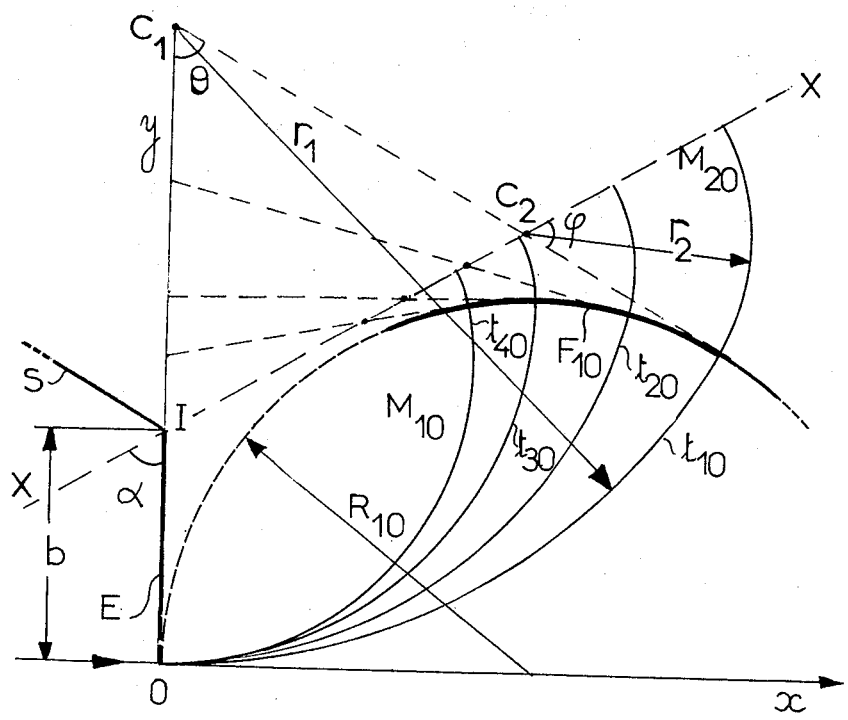
FIG. 4 shows the paths of the particles in the device of FIG. 3.

FIG. 4 shows in detail the different paths of the particles having different momentum in the deflection device shown in FIG. 3. In this embodiment, the ratio b/R has been chosen equal to 0.63, b being the distance separating the mean path of incident beam $f_i$ from point I, the intersection of axis XX with the input face E of the deflection device. For the different paths shown $t_{10}$, $t_{20}$, $t_{30}$, $t_{40}$, the centers of curvature $C_2$ in magnetic sector $M_{20}$ are substantially placed on the axis of symmetry XX. These different paths $t_{10}$, $t_{20}$ . . . correspond to energy particles respectively equal to $E_{10}$, $E_{20}$, $E_{30}$, $E_{40}$.

Figure 6:
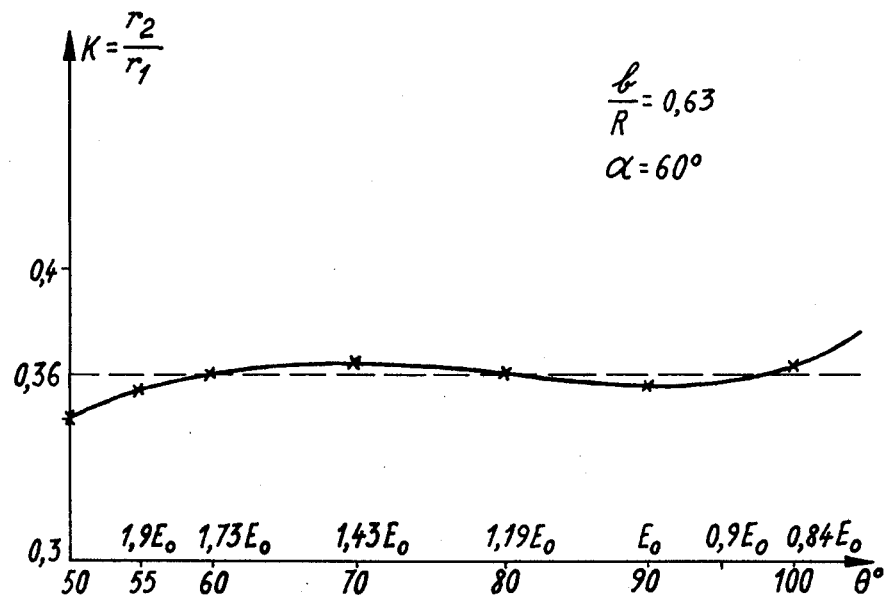

FIG. 6 shows the variations of $K=(r_2/r_1)$ as a function of $\theta$. It may be noted that, in this embodiment (FIG. 3) K is substantially equal to 0.36 for values $\theta$ between 55° and 100° and the magnetic inductions created in the air gaps of magnetic sectors $M_{10}$, $M_{20}$ and $M_{30}$ are respectively equal to 0.36 $B_o$, $B_o$ and 0.36 $B_o$.

In the embodiments shown in FIGS. 1 and 3, the differences in value of the magnetic inductions in sectors $M_1$, $M_3$ and sector $M_2$ have been obtained with different heights of the air gaps of these magnetic sectors.

Figure 7:
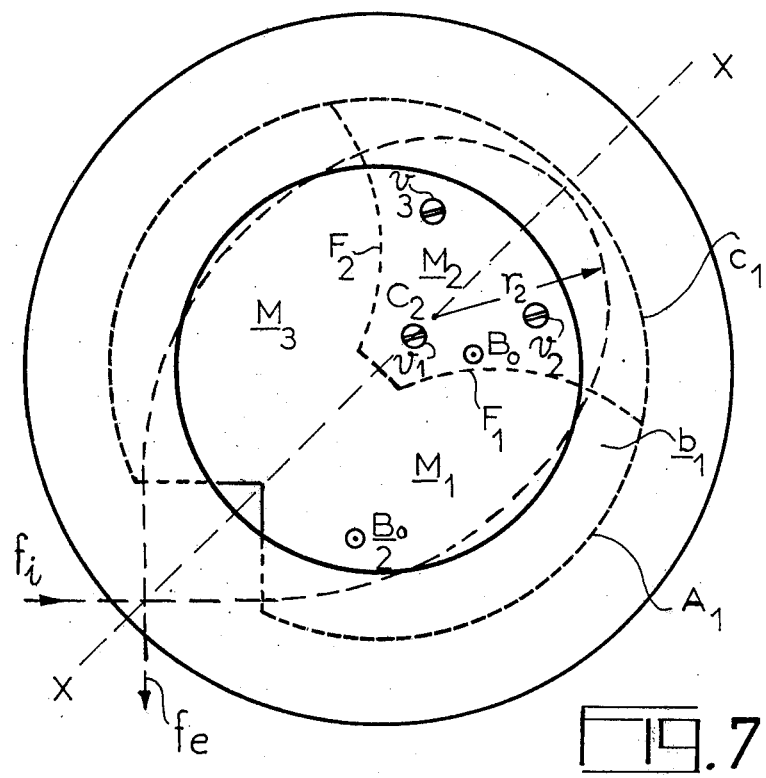
FIGS. 7 and 8 show respectively a top view and a sectional view along the axis of symmetry XX of a pair of pole pieces used in the device of the invention.
Figure 8:
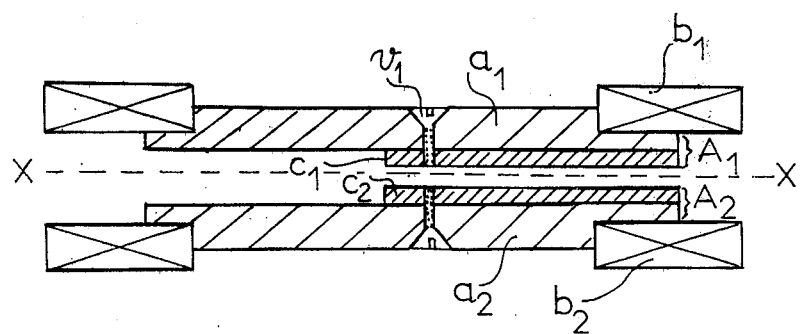

In FIG. 7 there is shown an embodiment of a pole piece $A_1$ in accordance with the invention and the magnetic coil which is associated therewith. Pole piece $A_1$, circular in shape, is formed by an element $a_1$ (FIG. 8) made from magnetic material, soft iron for example, whose dimensions are defined by the operating characteristics of the deflection device (type of particles, energy of these latter, value of the magnetic inductions used), and by an element $c_1$ superimposed on element $a_1$ and fixed to this latter by means of three screws $v_1$, $v_2$, $v_3$ for example, this element $c_1$ delimiting the intermediate magnetic sector $M_2$ (or $M_{20}$). The thicknesses of elements $a_1$ and $c_1$ are chosen with respect to the value of the magnetic inductions used in magnetic sectors $M_1$, $M_2$, $M_3$ (or $M_{10}$, $M_{20}$, $M_{30}$) so as to avoid any saturation of the magnetic material forming pole piece $A_1$. An annular magnetic coil $b_1$ is disposed on pole piece $A_1$. Opposite pole piece $A_1$ is placed an identical pole piece $A_2$, associated with the annular magnetic coil $b_2$ identical to $b_1$ (FIG. 8).

In operation, in the embodiments shown in FIGS. 1 and 3 of the device of the invention, the different paths of the particles converge in the horizontal plane H in a focus $F_H$ situated on the output face S of the third magnetic sector $M_3$ (FIG. 9) whereas in the vertical plane V, the whole of the deflection device behaves like a creeping space. If it is desired to obtain a stigmatic magnetic deflection system, i.e. for forming a pinpoint image of an object point situated outside the axis of the incident beam $f_i$, the divergences of the beam must be compensated for both in the vertical plane V and the horizontal plane H. For that, it is sufficient for the mean path of incident beam $f_i$ to form with the input face E of the magnetic deflection device an angle a little different from $\pi/2$ (FIG. 10).

Figure 9:
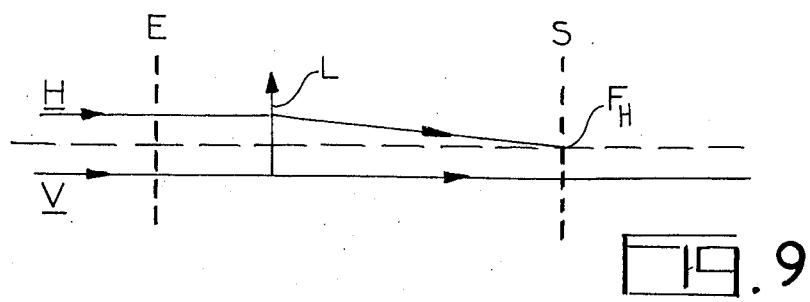
FIG. 9 shows the lens effect obtained in the horizontal plane with the devices of FIGS. 2 and 3.

FIG. 9 shows the lens effects obtained with a magnetic deflection device whose input E and output S faces are orthogonal to the mean path of the beam of particles.

Figure 10:
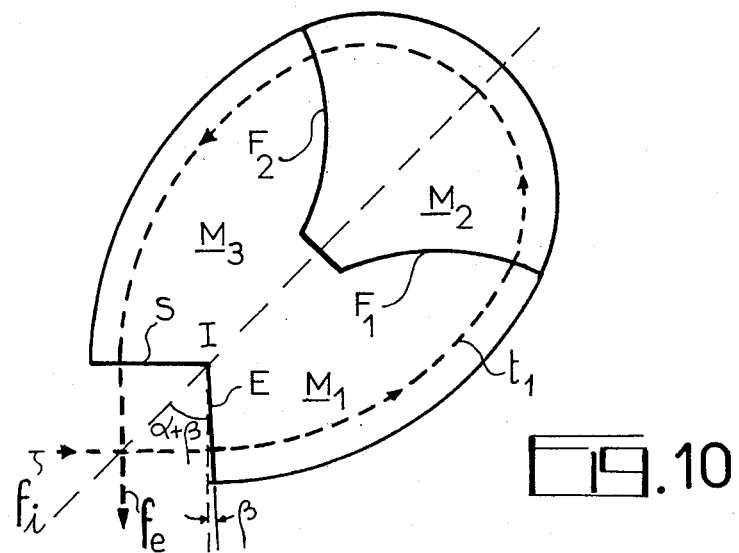
FIGS. 10 and 11 show respectively a variation of the device of the invention and the lens effects of this device on the beam, in the horizontal and vertical planes.
Figure 11:
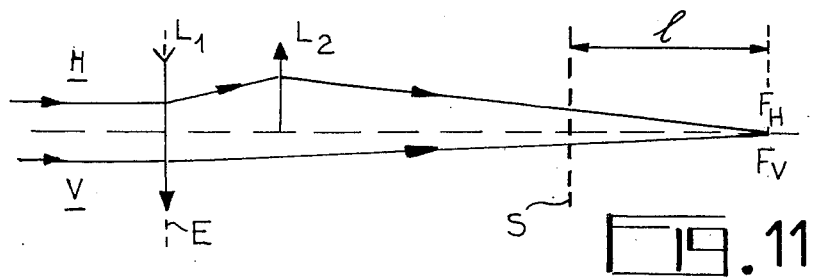

FIG. 11 shows the action of the magnetic lenses formed by the magnetic deflection device of the invention, shown in FIG. 10, when this deflection device presents to the beam an input face E forming an angle a little different from $\pi/2$ with the mean path of this incident beam $f_i$. In this case, the beam $f_i$ is subjected to focusing both in the horizontal plane H and in the vertical plane V, this double focusing being situated at a distance 1 from the output face S of the deflection device, this distance 1 corresponding for example to the distance separating the output face S of the deflecton device and a target Q intended to be bombarded by a substantially pinpoint beam.

The examples given are not limiting. In particular, the construction of the intermediate magnetic sector $M_2$ (or $M_{20}$) may be different from the examples given. It may in particular form a separate element which will be joined to the end sectors $M_1$, $M_3$ (or $M_{10}$, $M_{30}$).

The magnetic deflection device of the invention presents several advantages. It is compact and simple to construct. Furthermore, it has a wide passband. It may be advantageously used in radiotherapy apparatus, doing away with the need to adjust the magnetic field for a wide energy range of particles.

It is apparent that within the scope of the invention, modifications and different arrangements can be made other than are here disclosed. The present disclosure is merely illustrative with the invention comprehending all variations thereof.

What I claim is:
1. A device for the achromatic magnetic deflection of a beam of charged accelerated particles, comprising at least one electromagnet having pole pieces delimiting air gaps in which are created magnetic fields having the same direction and specific values so as to obtain paths of particles having the form of loops whose lengths are a function of the momentum of the particles, said pole pieces forming a first, a second and a third magnetic sector disposed one after the other and joined together, the whole of these magnetic sectors having a plane of symmetry perpendicular to the plane of the mean path of said beam of particles, and intersecting this plane along an axis XX, forming an axis of symmetry, and magnetic deflection device presenting successively to the beam of particles a flat input face E, a first curved face $F_1$, a second curved face $F_2$ and a flat output face S, said input E and output S faces forming therebetween an angle $2\alpha$, said identical curved faces $F_1$ and $F_2$ as well as said axis of symmetry XX being substantially orthogonal to the different paths of said particles, the values of said magnetic inductions created in the first and third magnetic sectors being respectively equal to $KB_o$, $B_o$ being the value of the magnetic induction in the second magnetic sector and K a numerical co-efficient less than 1.

2. A magnetic deflection device as claimed in claim 1, wherein the radius of curvature $r_1$ of the paths of the particles in the first and third magnetic sectors and the radius of curvature $r_2$ of the paths in the second intermediate magnetic sector are bound by the relationship:

$$\frac{r_2}{r_1} = K = 1 + \frac{\frac{B}{R}(\tan\theta - 1)\tan\alpha}{\cos\theta \tan\alpha + \sin\theta}$$

$r_1$ and $r_2$ depending, for specific magnetic induction values in the different magnetic sectors, on the momentum of said particles, b being the distance separating the mean incident path from the intersection point I of input face E with the axis of symmetry XX of the magnetic deflection device, $\theta$ being the total angle of deflection of the particles in the first and third magnetic sectors, this angle $\theta$ depending on the momentum of said particles, for specific values of the magnetic induction, R being the radius of curvature of curved faces $F_1$ and $F_2$ respectively common to the first and second magnetic sectors, and to the second and third magnetic sectors, and wherein the deflection angle $2\phi$ of the particles in the second magnetic sector is equal to $2[\pi-(\alpha+\theta)]$.

3. A magnetic deflection device as claimed in claim 2, wherein a pair of pole pieces is provided whose form and dimensions are such that they delimit three successive contiguous magnetic sectors $M_1$, $M_2$, $M_3$, in which are respectively created magnetic inductions of value $(B_o/2)$, $B_o$, $(B_o/2)$, the ratio $K=(r_2/r_1)$ being substantially equal to 0.5, wherein angle $2\alpha$ is substantially equal to $(\pi/2)$, and wherein the radius of curvature R of the intermediate faces $F_1$, $F_2$ is substantially equal to 2b.

4. A magnetic deflection device as claimed in claim 3, wherein the air gap of the magnetic sector $M_2$ has a height equal to half of the height of magnetic sectors $M_1$ and $M_3$.

5. A magnetic deflection device as claimed in claim 3, wherein the angles $\theta$ corresponding to the different paths are between 60° and 110°.

6. A magnetic deflection device as claimed in claim 2, wherein a pair of pole pieces are provided whose form and dimensions are such that they delimit three successive contiguous magnetic sectors $M_{10}$, $M_{20}$, $M_{30}$, in which are created respectively magnetic fields of values substantially equal to 0.36 $B_o$, $B_o$, 0.36 $B_o$, the ratio $(r_2/r_1)$ of the radius of curvature $r_2$ of the paths in magnetic sector $M_{20}$ and of the radius of curvature $r_1$ of the paths in magnetic sectors $M_{10}$ and $M_{30}$ being substantially equal to 0.36, said angle $\alpha$ being substantially equal to $\pi/3$, and said radius of curvature $R_{10}$ of the intermediate faces $F_{10}$, $F_{20}$ being substantially equal to 1.58 b.

7. A magnetic deflection device as claimed in claim 6, wherein the height of the air gap of magnetic sector $M_{20}$ is substantially equal to a third of the height of magnetic sectors $M_{10}$ and $M_{30}$.

8. A magnetic deflection device as claimed in claim 6, wherein the angles of rotation $\theta$ of the particles of different energies in magnetic sectors $M_{10}$ and $M_{30}$ are between 55° and 100°.

9. A magnetic deflection device as claimed in 3, wherein each of the pole pieces is formed by a first element $a_1$, made from a magnetic material on which is fixed a second element c placed so as to reduce the air gap of the pole pieces corresponding to said intermediat magnetic sector and having the form of the intermediate magnetic sector.

10. A magnetic deflection device as claimed in claim 6, wherein each of the pole pieces is formed by a first element $a_1$ made from a magnetic material on which is fixed a second element c placed so as to reduce the air gap of the pole pieces corresponding to the intermediate magnetic sector and having the form of said intermediate magnetic sector.

* * * * *